United States Patent [19]

Ando et al.

[11] 4,259,446

[45] Mar. 31, 1981

[54] PROCESS FOR PREPARATION OF DEOXYRIBONUCLEASES

[75] Inventors: Tadahiko Ando; Takehiko Shibata, both of Tokyo; Eiji Hayase, Niiza; Shukuko Ikawa, Wako, all of Japan

[73] Assignee: Rikagaku Kenkyusho, Wako, Japan

[21] Appl. No.: 58,802

[22] Filed: Jul. 19, 1979

[30] Foreign Application Priority Data

Jul. 28, 1978 [JP] Japan .................................. 53/92094

[51] Int. Cl.$^3$ ........................ C12N 9/22; C12N 15/00
[52] U.S. Cl. .................................... 435/199; 435/172
[58] Field of Search ................................ 435/199, 172

[56] References Cited

U.S. PATENT DOCUMENTS

| 3,930,956 | 1/1976 | Juni ................................... 435/172 X |
| 4,080,261 | 3/1978 | Shibata et al. .................... 435/172 X |
| 4,161,424 | 7/1979 | Ando et al. ......................... 435/199 |

Primary Examiner—Lionel M. Shapiro
Attorney, Agent, or Firm—Bucknam and Archer

[57] ABSTRACT

Disclosed is a process for the preparation of deoxyribonucleases (DNases) which comprise culturing a novel transformant belonging to the genus Bacillus, collecting a cell-free extract from cells obtained during a period ranging from the late logarithmic growth phase to the initial stage of the stationary growth phase, and subjecting said cell-free extract to fractionation or separation to obtain two or more DNases each of which possessing different substrate specificity.

5 Claims, No Drawings

PROCESS FOR PREPARATION OF DEOXYRIBONUCLEASES

BACKGROUND OF THE INVENTION (1) Field of the Invention

The present invention relates to a process for the preparation of novel DNases which involves culturing a novel transformant belonging to the genus Bacillus and collecting simultaneously at least two or more DNases possessing different substrate specificity, that is, the enzymes property of recognizing a specific nucleotide sequence of deoxyribonucleic acid and cleaving its bonds to produce unique fragments of the deoxyribonucleic acid.

(2) Description of the Prior Art

Enzymes (DNase) which decompose deoxyribonucleic acid (DNA), exist in various living things, and participate in important life processes, such as metabolism, decomposition, synthesis and recombination. Accordingly characteristics of enzyme particularly, in the field of protein chemistry and biological functions of these enzymes have recently attracted attention in the art.

In the study of the structure and function of the genes, it is important to produce and separate enzymes having specific actions, and deoxyribonucleic acid decomposing enzymes are valuable as biochemical reagents for molecular cloning of the genes and breed improvement.

DNases are roughly classified into two types, namely, exonucleases and endonuclease, according to their mode of action. More specifically, the former enzyme acts on a polynucleotide from its terminal and successively liberates nucleotide or oligonucleotide. The latter enzyme cleaves phosphodiester bonds in the DNA molecule.

In the field of endonuclease type enzymes, great progress has recently been made in the studies on enzymes showing a specificity of the structure of DNA particularly of the configuration of nucleotide or to the structural change which exists in nature or is introduced artificially, enzymes capable of recognizing structure of molecule and acting thereon and enzymes having a biologically important function (see Tadahiko Ando, Chemistry and Life, 13, 6, p. 342, 1975).

The present inventors have carried out research on enzymes and already established a process for production of an enzyme, which does not act on double-stranded DNA but specifically decomposes single-stranded DNA, from a culture broth of *Aspergillus oryzae* (see Japanese Pat. No. 593,368), a process for producing an enzyme capable of preferentially cleaving a purine-purine linkage in the DNA molecule, from cells of *Aspergillus oryzae* (see Japanese Pat. No. 621,205), a process for producing an enzyme capable of introducing single-strand breaks in DNA from bacteriophage-infected *Escherichia coli* (see Japanese Pat. No. 764,919), a process for producing an enzyme capable of acting on RNA and giving nucleoside cyclic phosphate from *Escherichia coli* by infection or induction with bacteriophage (see Japanese Pat. No. 829,334), a process for producing an enzyme capable of preferentially cleaving a guanine-guanine linkage in the DNA molecule from a culture broth of an alkalophilic bacteria (see Japanese Pat. No. 831,171), a process for producing from cells of *Bacillus subtilis,* an enzyme capable of specifically decomposing RNA moiety of DNA-RNA hybrid (see Japanese Pat. No. 877,668), and a process for producing an enzyme from *Bacillus subtilis* or and related strains belonging to the genus Bacillus having a substrate specificity to DNA: this enzyme recognises and cleaves specific nucleotide sequence (see Japanese Patent Application No. 121671/75 (Laid-Open Specification No. 47980/77) and Japanese Patent Application No. 87883/76 (Laid-Open Specification No. 15491/78)).

Microorganisms have a capability of specifically recognizing and decomposing foreign DNA in the cell (restriction system) and also have a capability of modifying such DNA so that the DNA shows a resistance to its own restriction system (modification system).

The restriction enzyme is an endonuclease participating in this restriction-modification system, and the restriction enzyme includes an enzyme capable of recognizing a specific sequence of 4 to 6 nucleotides in the molecule of a double-standard DNA and cleaving the sequence or in the vicinity of the sequence.

By virtue of such substrate specificity, these restriction enzymes can be effectively utilized for the studies on analysis of primary structure of DNA (nucleotide sequence) and its function and on in vitro recombination of heterogenous DNA.

The present invention provides an industrial process for the production of these restriction enzymes which are valuable as biochemical reagents.

The present inventors have carried out research on production, separation and substrate specificity of restriction enzymes prepared from microorganisms belonging to the genus Bacillus. We have succeeded in developing a process in which *Bacillus subtilis marburg* 168 (GSY 1026) as a recipient is subjected to transformation with DNA of *Bacillus subtilis* R to introduce the restriction-modification system of the strain R into the recipient, the resulting transformant ISMR 4 is selected, the selected transformant ISMR 4 as a recipient is subjected to transformation with DNA of *Bacillus subtilis* IAM 1247 to introduce the restriction-modification system of the strain 1247 into the recipient, the resulting transformant ISMRB 9 is selected, the selected transformant ISMRE 9 as a recipient is similarly subjected to transformation with DNA of *Bacillus subtilis IAM* 1231 to introduce the restriction-modification system of the strain 1231, and the resulting transformants ISMRBE 17 and ISMBF 21 are selected.

The above-mentioned transformant ISMRB 9 has restriction-modification systems of the strains GSY 1026, R and IAM 1247 in combination. We further succeeded in developing a process in which the transformant ISMRB 9 is cultured and a restriction enzyme Bsu R inhered in the strain R and a restriction enzyme Bsu 1247I inhered in the strain IAM 1247 are simultaneously prepared from cells of the transformant ISMRB 9.

Similarly, it has been confirmed that the transformant ISMRBE 17 has restriction-modification systems of the strains GSY 1026, R and IAM 1247 and a second restriction-modification system of the strain IAM 1231 in comibination, and that the transformant ISMBR has restriction-modification systems of the strains GSY 1026 and IAM 1247 and a second restriction-modification system of the strain IAM 1247.

Based on the foregoing findings, we have succeeded in simultaneously preparing three enzymes, that is, restriction enzymes Bsu R, Bsu 1247I and Bsu 1231 I inhered in the strains R, 1247 and 1231, respectively, by culturing the above-mentioned transformant ISMRBE 17.

We have also succeeded simultaneously preparing restriction enzymes Bsu 1247I and Bsu 1231II inhered in the strains IAM 1247 and IAM 1231 by culturing the above-mentioned transformant ISMBF 21.

Similarly, we have succeeded in developing a process in which the strain GSY 1012 derived from the above-mentioned strain GSY 1026 is used as a recipient and subjected to transformation with DNA of the above-mentioned strain IAM 1231 to introduce the restriction-modification systems of the strain IAM 1231, the resulting transformants ISE 15 and ISF 18 then being selected.

The transformant ISE 15 has a first restriction-modification system inhered in the strain IAM 1231. We have succeeded in preparing a restriction enzyme Bsu 1231I inhered in the strain IAM 1231 from cells obtained by culturing the transformant ISE 15.

The transformant ISF 18 has a second restriction-modification system inhered in the strain IAM 1231. We have succeeded in preparing a restriction enzyme Bsu 1231 II inhered in the strain IAM 1231 from cells obtained by culturing the transformant ISF 18.

Similarly, we have succeeded in developing a process in which the strain GSY 1012 derived from the strain GSY 1026 is used as a recipient and subjected to transformation with DNA of the abovementioned strain IAM 1247 to introduce the restrictionmodification system of the strain IAM 1247 into the recipient, the resulting transformant ISB 8 then being selected. This transformant ISB 8 has a restriction-modification system of the strain IAM 1247.

We have succeeded in preparing a restriction enzyme Bsu 1247I inhered in the strain IAM 1247 from cells obtained by culturing the above-mentioned transformant ISB 8.

We have now completed the present invention based on the foregoing achievements.

SUMMARY OF THE INVENTION

In accordance with the present invention, there is provided a process for the preparation of DNases which involves culturing a transformant belonging to the genus Bacillus, collecting a cell-free extract from cells obtained by the culturing, and subjecting the cell-free extract to fractionation and/or separation, thereby to obtain two or more DNases differing in substrate specificity from the transformant.

DETAILED DESCRIPTION OF THE INVENTION

The microorganism that is used in the present invention is a novel transformant belonging to the genus Bacillus, in which a restriction endonuclease-producing capability has been introduced by transformation.

By the term "transformation" is meant a method in which a genetically established microoganism is used as a recipient and the recipient is contacted with DNA prepared from a microorganism having a restriction-modification system different from that of the recipient to introduce a novel restriction-modification system into the recipient.

As the transformants that can be effectively used in the present invention, there can be mentioned (i) *Bacillus subtilis* ISMRB 9, (ii) *Bacillus subtilis* ISMRBE 17, (iii) *Bacillus subtilis* ISMBF 21, (iv) *Bacillus subtilis* ISE 15, (v) *Bacillus subtilis* ISF 18 and (vi) *Bacillus subtilis* ISB 8.

The foregoing transformants (i) through (vi) were deposited with the Fermentation Research Institute, Agency of Industrial Science and Technology, Ministry of International Trade and Industry, Japan (hereinafter referred to as "FERM") and the American Type culture Collection, 12301, Parklawn, Drive, Rockville, Md. 20852, USA under the following deposition numbers: and are on deposit with ATCC in an unrestricted deposit permitting the public full access to the culture:

| No. | | FERM-P No. | ATCC-No. |
| --- | --- | --- | --- |
| (i) | *Bacillus subtilis* ISMRB 9 | 4543 | 31526 |
| (ii) | *Bacillus subtilis* ISMRBE 17 | 4381 | 31522 |
| (iii) | *Bacillus subtilis* ISMBF 21 | 4384 | 31525 |
| (iv) | *Bacillus subtilis* ISE 15 | 4380 | 31527 |
| (v) | *Bacillus subtilis* ISF 18 | 4382 | 31523 |
| (vi) | *Bacillus subtilis* ISB 8 | 4383 | 31524 |

The applicant will maintain the deposition of ATCC 31526, 31522, 31525, 31527, 31523, and 31524 in the unristricted form until the end of the duration of a patent granted on this application if a patent is granted on this application, and thus said microorganism strains will be available to any third party at any time until the end of the duration of the patent granted on this application.

An instance of the method for obtaining the above-mentioned transformants from microoganisms belonging to the genus Bacillus will now be described. The method for obtaining the transformants is of course not limited to the one described below and various modifications and changes may be made according to known techniques, and these modifications and changes are included within the scope of the present invention.

*Bacillus subtilis marburg* 168GSY 1026 (ATCC No. 31339, FERM-P No. 4216) as a recipient was cultured at 37° C. with shaking in Bott's culture medium (composed of 50 µg/ml each of histidine, tryptophan, arginine, valine, lysine, glycine, asparagine, methionine and threonine, 0.6% $KH_2PO_4$, 1.4% $K_2HPO_4$, 0.1% sodium citrate, 0.2% ammonium sulfate, 0.5% of glucose and 6.5 mM $MgSO_4$) supplemented with 20 µg/ml each of adenine, leucine and methionine, until the cell number was increased to $4\times10^8$ per ml. Then, 0.1 ml of DNA (45 µg/ml) of *Bacillus subtilis* R (see S.Bron et al., Molec. Gen. Genet., 143, 13–23, 1975) obtained by the phenol extraction method at pH 9 was added to the culture broth, and incubation was continued at 37° C. for 30 minutes with shaking. The cultured broth was diluted 10 times with the same culture medium, and incubation was continued at 30° C. with shaking overnight. The cultured broth was diluted 1 to 100 times with the same culture medium and a plate of a TYP culture medium (containing 1% of bactotryptone, 0.5% of yeast extract, 1% of NaCl and 1.5% of agar) in which phage φ105C 168 propagated by *Bacillus subtilis marburg* 168GSY 1026 had been shown in advance was inoculated with the above dilution. Culturing was conducted at 37° C. overnight and a colony of the resultant transformant having a resistance to phage φ105C 168 was collected. Thus, a transformant ISMR4 having restriction-modification system of *Bacillus subtilis marburg* 168GSY 1026 and *Bacillus subtilis* R was obtained.

A transformant ISMRB 9 having the restriction-modification systems of *Bacillus subtilis marburg* 168GSY 1026 and *Bacillus subtilis* R and one restriction-modification system of *Bacillus subtilis* IAM 1247 can be obtained and separated according to the above-mentioned method by using the above-mentioned transformant ISMR4 as a recipient and DNA of *Bacillus subtilis* IAM 1247.

Furthermore, a transformant ISMRBE 17 having the restriction-modification systems of *Bacillus subtilis marburg* 168GSY 1026, *Bacillus subtilis* R and *Bacillus subtilis* IAM 1247 and *Bacillus subtilis* IAM 1231 and a transformant ISMBF 21 having the restriction-modification systems of *Bacillus subtilis* 168GSY 1026, *Bacillus subtilis* IAM 1231 and *Bacilus subtilis* IAM 1247 can be obtained according to the above-mentioned method by using the above transformant ISMRB 9 as a recipient and DNA of *Bacillus subtilis* IAM 1231.

Still further, a transformant ISE 15 having the first restriction-modification system of *Bacillus subtilis* IAM 1231 and a transformant ISF 18 having the second restriction-modification system of *Bacillus subtilis* IAM 1231 can be obtained according to the above-mentioned method by using *Bacillus subtilis* 168GSY 1012 derives from *Bacillus subtilis marburg* 168GSY 1026 as a recipient and DNA of *Bacillus subtilis* IAM 1231.

Moreover, a tranformant ISB 8 having the restriction-modification system of *Bacillus subtilis* IAM 1247 can be obtained according to the above-mentioned method by using said strain 168GSY 1012 as a recipient and DNA of *Bacillus subtilis* IAM 1247.

Each of the foregoing transformants (i) through (vi) is obtained by introducing a restriction-modification system of a known strain belonging to the genus Bacillus into *Bacillus subtilis marburg* 168GSY 1026 or *Bacillus subtilis marburg* 168GSY 1012 derived from the strain 168GSY 1026 by using DNA of said known strain. Basic microbiological properties of these transformants are the same as those of the basic recipient, that is, *Bacillus subtilis marburg* 168GSY 1026.

Characteristic microbiological properties of this strain 168GSY 1026, determined according to the methods described by R. E. Gordon, W. C. Haymes and C. H-N. Pang in "The Genus Bacillus", U.S. Dept. Agr., 1974 and "Bergey's Manual of Determinative Bacetriology", 1974, are as follows.

(A) Morphology:
The strain is in the form of a vegatative rod, has peritrichous flagella and exhibits a moving property. The size $(0.7-0.9\mu) \times (1.8-3.0\mu)$.
The gram stainability is positive.
(B) Growth on Culture Media:
(1) Bouillon-agar plate culture: good growth
(2) Bouillon-agar streak culture: good growth
(3) Bouillon liquid culture: good growth
(4) Glucose bouillon culture: good growth
(5) Glucose bouillon-agar culture: More spreading and smooth growth than in bouillon-agar culture
(C) Physiological Properties:
(1) Growth conditions:
Temperature: 18°–50° C.
Optimum temperature: 30°–45° C.
pH: 5 to 8
Optimum pH: 7.0–7.5
(2) Nitrate reduction: positive
(3) Hydrolysis of gelatin and casein: positive
(4) Hydrolysis of starch: positive
(5) Salt resistance: good growth in 5% NaCl solution (6) Requirement of oxygen: aerobic When the above bacteriological properties are examined with reference to the above-mentioned literature references and "Transformation and Transduction in Defective Mutants of *Bacillus subtilis*", Journal of Bacteriology, 93, 1925–1937, 1967, it is confirmed that the microorganism is a known marburg strain belonging to *Bacillus subtilis*.

Results of examinations made on restriction-modification systems of the foregoing transformants (i) through (vi) using phage $\phi$105C are shown in Table 1.

TABLE 1

| Transformant | Restriction-Modification System | Introduced Restriction-Modification Systems of Other Bacillus Strains | | | | | |
|---|---|---|---|---|---|---|---|
| | | 168 | R | 1247 I | 1247 II | 1231 I | 1231 II |
| ISMR 4 | restriction | + | + | − | − | − | − |
| | modification | + | + | − | − | − | − |
| ISMRB 9 | restriction | + | + | + | − | − | − |
| | modification | + | + | + | − | − | − |
| ISMRBE 17 | restriction | + | + | + | − | + | − |
| | modification | + | + | + | − | + | − |
| ISMBF 21 | restriction | + | − | + | − | − | + |
| | modification | + | − | + | − | − | + |
| ISE 15 | restriction | − | − | − | − | + | − |
| | modification | + | − | − | − | + | − |
| ISF 18 | restriction | − | − | − | − | − | + |
| | modification | + | − | − | − | − | + |
| ISB 8 | restriction | − | − | + | − | − | − |
| | modification | + | − | + | − | − | − |

Culturing of the foregoing transformants (i) through (iv) can be performed according to known culturing methods. A typical culturing method will now be described, though culturing methods applicable in the present invention are in no way limited by this method.

A culture medium containing an amino acid, a casein decomposition product, glucose, a phosphate, a sulfate, yeast extract and the like is inoculated with the transformant and culturing is carried out at 30° to 37° C. with aeration and agitation. Cells are collected during a period ranging from the logarithmic phase to the initial stage of the stationary phase. The cells are subjected to ultrasonic pulverization and centrifugal separation as they are or after they are subjected to lysozyme treatment to prepare a protoplasts, whereby a cell-free extract is obtained. The obtained cell-free extract is subjected to fractionation and streptomycin sulfate treatment. At least two endonuclease type DNases differing in substrate specificity, selected from the above-mentioned Bsu R, Bsu 1247 I, Bsu 1231 I and Bsu 1231 II, are simultaneously obtained after appropriate purification, such as by gel filtration using Ultragel ACA 44 or Sephadex G-100, ion-exchange chromatography using DEAE cellulose or phosphocellulose or a combination thereof.

Each of the enzymes obtained according to the process of the present invention is a known endonuclease type DNA decomposing enzyme.

Physicochemical properties of these enzymes will now be described. (Physicochemical Properties of Enzymes)

(1) Measurement of Activity of Endonuclease:
Phage $\phi$105C is propagated in a host strain and phage $\phi$105C DNA which has undergone host-dependent modification is separated and prepared. This phage $\phi$105C DNA is used as a substrate for measurement of the enzymatic activity. More specifically, phage $\phi$105C DNA formed by using *Bacillus subtilis marburg*

168GSY 1026 as the host strain and phage φ105C DNA formed by using the transformant ISMRB 9 as the host strain are used as substrates.

An enzymatic reaction liquid comprising 0.1 μg of the substrate DNA, 50 nM tris-HCl buffer solution (pH=7.5), 10 mM MgCl₂, 1 mM 2-mercaptoethanol, 1% of gelatin and an enzyme sample is treated at 37° C. for 50 minutes, 30 μl of the resulting liquid reaction mixture is subjected to electrophoresis at 110 V for 1.5 to 2 hours by using a plate of 1% agarose gel and dipped in a solution containing 0.5 μ/ml of ethidium bromide, and the fluorescence is photographed under irradiation of ultraviolet rays. The restriction enzymatic activity is determined based on the position and number of DNA fragments detected in the obtained photo.

(2) Characteristics of Enzymes (Substrate Specificity):

(a) Restriction enzyme Bsu R:

This enzyme is a DNase separated from *Bacillus subtilis* R. It recognizes the following nucleotide sequence in the molecule of DNA:

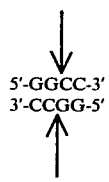

5'-GGCC-3'
3'-CCGG-5' and cleaves the sequence at the part ↓.

Furthermore, this enzyme cleaves SV40 DNA (tumor virus (Simian Virus 40)) at 18 points, λ phage DNA at more than 200 points, λ dv DNA at 14 points and phage SPP1 DNA at more than 80 points (see S. Bron, K. Murray and T. A. Trautner, Mol. Gen. Genet., 143, 13 (1975), S. Bron and K. Murray, Mol. Gen. Genet., 143, 25 (1975), and Tadahiko Ando and Takehiko Shibata, Proteins, Nucleic Acids and Enzymes, 22, (8), 1012 (1977)).

(b) Restriction enzyme Bsu 1247 I:

This enzyme is a DNase separated from *Bacillus subtilis* IAM 1247. It recognizes the following nucleotide sequence in the molecule of DNA:

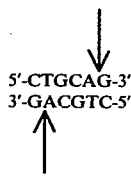

5'-CTGCAG-3'
3'-GACGTC-5' and cleaves the sequence at part ↓.

The enzyme cleaves λ phage DNA at 18 points, SV40 DNA at 3 points and phage φ105C DNA (see T. Shibata, S. Ikawa, C. Kim and T. Ando, J. Bacteriol., 128, 473 (1976), Tadahiko Ando and Takehiko Shibata, Proteins, Nucleic Acids and Enzymes, 22 (8), 1012 (1977 and Japanese Patent Application No. 87883/76 (Laid-Open Specification No. 15491/78)).

(c) Restriction enzyme Bsu 1231 I:

This enzyme is a DNase separated from *Bacillus subtilis* IAM 1231. The nucleotide sequence to be cleft in the molecule of DNA by this enzyme is unknown. However, it has been confirmed that this enzyme cleaves λ phage DNA, phage φ105C DNA and phage SPP1 DNA (see T. Shibata, S. Ikawa, C. Kim and T. Ando, J. Bacteriol., 128, 473 (1976), Tadahiko Ando and Takehiko Shibata, Proteins, Nucleic Acids and Enzymes, 22, (8), 1012 (1977) and Japanese Patent Application No. 87883 (Laid-Open Specification No. 15491/78).

(d) Restriction enzyme Bsu 1231 II:

This enzyme is a DNase separated from *Bacillus subtilis* IAM 1231. The nucleotide sequence to be cleft in the molecule of DNA by this enzyme is unknown. However, it has been confirmed that this enzyme cleaves phage φ 105C DNA at about 15 points, λphage DNA at about 15 points, phage φ X174 DNA at about 5 points and ColEI (plasmid (cellular intrinsic factor of *Escherichia coli*)) at about 9 points.

The foregoing enzymes obtained according to the present invention are very valuable as biochemical reagents for clarifying the structure and function of DNA of the genes and molecular cloning in the genes.

The process of the present invention will now be described in detail with reference to the following Examples that by no means limit the scope of the invention.

EXAMPLE 1

The transformant ISMRB 9 (ATCC 31526) was precultured at 37° C. overnight in 1 liter of Bact-Penessary Broth medium (containing 1.5% beef extract, 1.5% yeast extract, 5% peptone, 1% glucose, 3.5% NaCl, 3.68% K₂HPO₄ and 1.32% KH₂PO₄). The culture broth was transferrred into 10 liter of a tryptone broth medium (containing 1% tryptone, 5% yeast extract and 10% NaCl) and culturing was conducted at 37° C. for 4 to 5 hours with aeration and agitation. Cells in the initial stage of the stationary growth phase were collected by centrifugal separation, and 30 g of the cells were suspended in 50 ml of buffer solution A (containing 10 mM tris-HCl buffer solution (pH=7.5), 0.1 mM MEDTA and 5 mM mercaptoethanol). The resulting suspension was mixed with glass beads (diameter=0.1 mm) and pulverization treatment was carried out at 0° C. for 15 minutes, and the pulverized suspension was centrifuged for 10 minutes at 10000 rpm.

To the obtained supernatant liquid was added

A solution of streptomycin sulfate so as to get 1.7, solution of the sulfate, and the mixture was fractionated into the precipitate and supernatant liquid by centrifugal separation. The precipitate fraction was suspended in the above-mentioned buffer solution A to which 0.2 M MgCl₂ had been added, and a supernatant liquid containing the restriction enzyme Bsu R was obtained.

Ammonium sulfate was added to the streptomycin supernatant liquid at a concentration corresponding to 40-80% saturation, and the resulting precipitate was suspended in the buffer solution A and dialyzed by the buffer solution A. The dialysis fraction was passed through a column packed with AcA 34 (2.2 cm×58 cm) and elution was carried out by using a buffer solution containing 1% glycerin and 0.3 M NaCl, and the activity of Bsu 1247 I was detected in 150 to 220 ml of the eluate.

Further, dialysis was carried out using a buffer solution containing 10% glycerin and the dialysis fraction was passed through an adsorption column packed with DE 52. The elution treatment was carried out using the buffer solution A containing 10% glycerin and having a linear NaCl concentration gradient of 0 to 0.5 M. Refined Bsu 1247 I was collected in the fraction eluted by the buffer solution A having an NaCl concentration of 0.12 to 0.2 M.

EXAMPLE 2

The transformant ISMRBE 17 (ATCC No. 31522) was cultured and treated in the same manner as described in Example 1, and the fraction containing the restiction enzyme Bsu R was collected from the streptomycin precipitate fraction.

The streptomycin supernatant liquid was treated in the same manner as in Example 1, and the activities of the restriction enzymes Bsu 1247 I and Bsu 1231 I were detected in 150 to 220 ml of the obtained eluate. This fraction was dialyzed by the buffer solution A containing 10% glycerin, and the dialysis fraction was passed through an adsorption column packed with DEAE cellulose and DE 52. Elution was carried out by the buffer solution A containing 10% glycerin and having a linear NaCl concentration gradient of 0 to 0.5 M. The fraction eluted by the buffer solution A having an NaCl concentration of 0.12 to 0.2 M was collected and dialyzed by a 10 mM potassium phosphate buffer solution (pH=6.8) containing 10% of glycerin, 0.1 mM EDTA and 5 mM 2-mercaptoethanol. The dialysis fraction was adsorbed by a column packed with phosphocellulose p-11 and elution was carried out by a solution of KCl having a linear concentration gradient of 0 to 0.6 M. Bsu 1247 I was collected in the fraction eluted by the KCl solution having a concentration of 0.22 to 0.32 M and Bsu 1231 I was collected in the fraction eluted by the KCl solution having a concentration of 0.20 to 0.38 M.

EXAMPLE 3

The transformant ISMBF 21 (ATCC No. 31525) was cultured and treated in the same manner as in Example 1 to obtain a streptomycin supernatant liquid. The activities of the restriction enzymes Bsu 1247 I and Bsu 1231 II were detected in 150 to 220 ml of a fraction obtained by treating the streptomycin supernatant liquid in the same manner as in Example 1. The so obtained fraction was treated in the same manner as in Example 2. More specifically, the fraction was dialyzed by the buffer solution A containing 10% glycerin and adsorbed in a column packed with DEAE cellulose and DE 52. Elution was carried out by using the buffer solution A containing 10% glycerin and having a linear NaCl concentration gradient of 0 to 0.5 M and the fraction eluted by the buffer solution A having a concentration of 0.12 to 0.2 M was collected. The fraction was further dialyzed by a 10 mM potassium phosphate buffer solution (pH=6.8) containing 10% glycerin, 0.1 M EDTA and 5 mM 2-mercaptoethanol. The dialysis fraction was adsorbed in a column packed with phosphocellulose P-11 and elution was carried out by a KCl solution having a linear concentration gradient of 0 to 0.8 M. Refined Bsu 1231 II was collected in the fraction eluted by the KCl solution having a concentration of 0.65 to 0.70 M and refined Bsu 1247 I was collected in the fraction eluted by the KCl solution having a concentration of 0.22 to 0.32 M.

EXAMPLE 4

The transformant ISE 15 (ATCC No. 31527) was cultured and treated in the same manner as in Example 1 to obtain a streptomycin supernatant liquid. The activity of the restriction enzyme Bsu 1231 I was detected in 150 to 220 ml of a fraction obtained by treating the streptomycin supernatant liquid in the same manner as in Example 1. The fraction was treated in the same manner as in Example 1. More specfically, the fraction was dialyzed by the buffer solution A containing 10% glycerin and then adsorbed in a column packed with DE 52. Elution was carried out using the buffer solution A containing 10% glycerin and having a linear NaCl concentration gradient of 0 to 0.5 M. Refined Bsu 1231 I was collected in the fraction eluted by the buffer solution A having an NaCl concentration of 0.12 to 0.18 M.

EXAMPLE 5

The transformant ISF 18 (ATCC No. 31523) was cultured and treated in the same manner as in Example 4. Refined Bsu 1231 II was collected in the fraction eluted by the buffer solution A having an NaCl concentration of 0.20 to 0.30 M.

EXAMPLE 6

The transformant ISB 8 (ATCC No. 31524) was cultured and treated in the same manner as in Example 4. Refined Bsu 1247 I was collected in the fraction eluted by the buffer solution A having an NaCl concentration of 0.12 to 0.20 M.

What is claimed is:

1. A process for the preparation of deoxyribonucleases which comprises culturing a transformant belonging to the genus *Bacillus*, collecting a cell-free extract from cells obtained by the culturing, subjecting said cell-free extract to fractionation and/or separation, wherein the cells are those obtained during a period ranging from the logarithmic growth phase to the initial stage of the stationary growth phase, thereby to obtain at least two deoxyribonucleases, each of which possessing different substrate specificity and they are at least two members selected from Bsu R, Bsu 1247 I, Bsu 1231 I and Bsu 1231 II, said deoxyribonucleases being restriction enzymes.

2. A process for the preparation of deoxyribonucleases which comprises culturing at least the transformant belonging to the genus Bacillus, which is a member selected from the group consisting of (i) *Bacillus subtilis* ISMRB 9, (ii) *Bacillus subtilis* ISMRBE 17, (iii) *Bacillus subtilis* ISMBF 21, (iv) *Bacillus subtilis* ISE 15, (v) *Bacillus subtilis* ISF 18 and (vi) *Bacillus subtilis* ISB 8, collecting a cell-free extract from cells obtained by the culturing, and subjecting said cell-free extract to fractionation and/or separation, thereby to obtain at least two deoxyribonucleases each of which possessing different substrate specificity.

3. A process for the preparation of deoxyribonuclease acid according to claim 2, wherein the cells are those obtained during a period ranging from the late logarithmic growth phase to the initial stage of the stationary growth phase.

4. A process for the preparation of deoxyribonucleic acid according to claim 2, wherein the fractionation and/or separation treatment is at leat one treatment selected from streptomycin treatment, ammonium sulfate fractionation, ion exchange chromatography, gel filtration and affinity chromatography.

5. A process for the preparation of deoxyribonucleases according to claim 2, wherein at least two deoxyribonucleases each of which possessing different substrate specificity are at least two members selected from Bsu R, Bsu 1247 I, Bsu 1231 I and Bsu 1231 II.

* * * * *